United States Patent
Koduri et al.

(10) Patent No.: US 9,364,714 B2
(45) Date of Patent: Jun. 14, 2016

(54) FUZZY LOGIC-BASED EVALUATION AND FEEDBACK OF EXERCISE PERFORMANCE

(71) Applicant: ZSOLUTIONZ, LLC, Sammamish, WA (US)

(72) Inventors: Sunil Koduri, Sammamish, WA (US); John Michael Hand, Sammamish, WA (US); Surendra P. S. Bhatia, Kent, WA (US); Bobby Joe Adams, Kirkland, WA (US); John W. Ransone, Wimberley, TX (US); Shalini Koduri, Sammamish, WA (US)

(73) Assignee: Zsolutionz, LLC, Sammamish, WA (US)

( * ) Notice: Subject to any disclaimer, the term of this patent is extended or adjusted under 35 U.S.C. 154(b) by 0 days.

(21) Appl. No.: 14/588,346

(22) Filed: Dec. 31, 2014

(65) Prior Publication Data
US 2015/0196805 A1    Jul. 16, 2015

Related U.S. Application Data

(60) Provisional application No. 61/927,399, filed on Jan. 14, 2014.

(51) Int. Cl.
*A63B 71/00*    (2006.01)
*A63B 24/00*    (2006.01)
(Continued)

(52) U.S. Cl.
CPC ........ *A63B 24/0087* (2013.01); *G06F 19/3481* (2013.01); *G06K 9/00335* (2013.01); *G06T 7/00* (2013.01)

(58) Field of Classification Search
CPC ........... A63B 24/0003; A63B 24/0006; A63B 24/0062; A63B 24/0075; A63B 2024/0015; A63B 2024/0068
See application file for complete search history.

(56) References Cited

U.S. PATENT DOCUMENTS

| D296,385 S | 6/1988 | Lenihan |
| D348,356 S | 7/1994 | Nemoto |

(Continued)

FOREIGN PATENT DOCUMENTS

| EP | 0569879 A2 | 11/1993 |
| EP | 1758040 | 2/2007 |

(Continued)

OTHER PUBLICATIONS

Office Action for U.S. Appl. No. 29/479,299, mailed on Jan. 7, 2015, Sunil Koduri, "Fitness Machine User Interface", 7 pages.

(Continued)

*Primary Examiner* — Oren Ginsberg
(74) *Attorney, Agent, or Firm* — Lee & Hayes, PLLC

(57) ABSTRACT

Disclosed herein are techniques and systems for evaluating exercise performance of a user of a fitness system by utilizing one or more intelligent sensors, including at least one camera-based sensor configured to detect image data of the user. The fitness system may include a stationary exercise device, a memory to store personal information about a user, and a processor to generate a set of exercise rules based, at least in part, on the personal information about the user. The fitness system may also include one or more sensors to monitor a physical state of the user, and a fuzzy system to generate an evaluation for the user based, at least in part, on i) the set of rules and ii) output from the one or more sensors. The fitness system may thereby provide real-time, constructive feedback regarding the user's exercise performance based on the sensed data.

34 Claims, 5 Drawing Sheets

(51) Int. Cl.
*G06F 19/00* (2011.01)
*G06K 9/00* (2006.01)
*G06T 7/00* (2006.01)

(56) References Cited

U.S. PATENT DOCUMENTS

| | | | |
|---|---|---|---|
| D350,135 S | 8/1994 | Polk, Jr. et al. | |
| 5,368,532 A | 11/1994 | Farnet | |
| 5,527,239 A | 6/1996 | Abbondanza | |
| 5,810,747 A | 9/1998 | Brudny et al. | |
| 5,947,868 A | 9/1999 | Dugan | |
| 6,126,572 A * | 10/2000 | Smith | A63B 21/002 482/4 |
| 6,152,856 A | 11/2000 | Studor et al. | |
| D470,785 S | 2/2003 | Vermillion | |
| 6,605,038 B1 | 8/2003 | Teller et al. | |
| D531,989 S | 11/2006 | Dayan | |
| D542,959 S | 5/2007 | Yao et al. | |
| 7,359,121 B2 | 4/2008 | French et al. | |
| D584,843 S | 1/2009 | Kosche | |
| D593,426 S | 6/2009 | Huang et al. | |
| D619,485 S | 7/2010 | Ikeda et al. | |
| D629,549 S | 12/2010 | Feigenbaum | |
| 7,914,420 B2 | 3/2011 | Daly et al. | |
| D636,769 S | 4/2011 | Wood et al. | |
| D637,751 S | 5/2011 | Chiu | |
| 8,007,405 B2 | 8/2011 | Burnfield et al. | |
| D650,357 S | 12/2011 | Chen | |
| 8,152,695 B2 | 4/2012 | Riley et al. | |
| 8,235,724 B2 | 8/2012 | Gilley et al. | |
| D678,271 S | 3/2013 | Chiu | |
| D684,968 S | 6/2013 | Smith et al. | |
| 8,537,568 B2 | 9/2013 | Tang | |
| D693,325 S | 11/2013 | Lee | |
| 8,597,142 B2 | 12/2013 | Mayles et al. | |
| 8,620,146 B1 | 12/2013 | Coleman | |
| D702,206 S | 4/2014 | Kim et al. | |
| D702,232 S | 4/2014 | Choi | |
| D705,777 S | 5/2014 | Groene et al. | |
| D706,773 S | 6/2014 | Lu | |
| D710,349 S | 8/2014 | Han et al. | |
| D711,258 S | 8/2014 | Jacobs et al. | |
| D711,871 S | 8/2014 | Daniel | |
| 8,803,888 B2 | 8/2014 | Buban | |
| D712,400 S | 9/2014 | Kim et al. | |
| D712,855 S | 9/2014 | Thompson et al. | |
| D712,899 S | 9/2014 | Park et al. | |
| D712,946 S | 9/2014 | Hong | |
| D714,746 S | 10/2014 | Euiseok et al. | |
| D714,782 S | 10/2014 | Ohshima | |
| D715,795 S | 10/2014 | McManigal | |
| D716,265 S | 10/2014 | Park et al. | |
| D716,293 S | 10/2014 | Hwang et al. | |
| D716,799 S | 11/2014 | Green et al. | |
| D718,303 S | 11/2014 | Choteau et al. | |
| D720,334 S | 12/2014 | Wang | |
| 2002/0055418 A1 | 5/2002 | Pyles et al. | |
| 2003/0109322 A1* | 6/2003 | Funk | A63B 24/0003 473/222 |
| 2004/0102931 A1* | 5/2004 | Ellis | A61B 5/1038 702/188 |
| 2005/0039541 A1 | 2/2005 | Kurono | |
| 2005/0070809 A1 | 3/2005 | Acres | |
| 2005/0272561 A1 | 12/2005 | Cammerata | |
| 2007/0123389 A1 | 5/2007 | Martin | |
| 2007/0232452 A1 | 10/2007 | Hanoun | |
| 2008/0300521 A1 | 12/2008 | Karkanias et al. | |
| 2008/0300914 A1* | 12/2008 | Karkanias | A63B 24/0084 705/2 |
| 2009/0069156 A1 | 3/2009 | Kurunmaki et al. | |
| 2009/0156363 A1 | 6/2009 | Guidi et al. |
| 2010/0280416 A1 | 11/2010 | Hyde et al. |
| 2010/0323846 A1 | 12/2010 | Komatsu et al. |
| 2011/0016120 A1 | 1/2011 | Haughay, Jr. et al. |
| 2011/0172060 A1 | 7/2011 | Morales et al. |
| 2011/0201476 A1 | 8/2011 | Solomon |
| 2012/0109013 A1 | 5/2012 | Everett et al. |
| 2012/0122529 A1 | 5/2012 | Lyons |
| 2012/0139727 A1 | 6/2012 | Houvener et al. |
| 2012/0183939 A1 | 7/2012 | Aragones et al. |
| 2012/0220428 A1 | 8/2012 | Carlson |
| 2012/0299846 A1 | 11/2012 | Matsuda |
| 2012/0310971 A1 | 12/2012 | Tran |
| 2012/0311334 A1 | 12/2012 | Bruestle et al. |
| 2013/0024408 A1 | 1/2013 | Firminger et al. |
| 2013/0090749 A1 | 4/2013 | Oswald et al. |
| 2013/0144411 A1 | 6/2013 | Savarese et al. |
| 2013/0178960 A1 | 7/2013 | Sheehan et al. |
| 2013/0225370 A1 | 8/2013 | Flynt et al. |
| 2013/0274066 A1 | 10/2013 | Ashby et al. |
| 2013/0307816 A1 | 11/2013 | Lee et al. |
| 2014/0249429 A1 | 9/2014 | Tran |
| 2014/0309082 A1 | 10/2014 | Iglehart |
| 2015/0196804 A1 | 7/2015 | Koduri et al. |
| 2015/0199494 A1 | 7/2015 | Koduri et al. |

FOREIGN PATENT DOCUMENTS

| | | |
|---|---|---|
| EP | 1978497 | 10/2008 |
| WO | WO9421171 A1 | 9/1994 |
| WO | WO2008007856 A1 | 1/2008 |
| WO | WO2013034987 A2 | 3/2013 |

OTHER PUBLICATIONS

Office Action for U.S. Appl. No. 14/588,289, mailed on Jul. 22, 2015, Sunil Koduri, "Sensor-Based Evaluation and Feedback of Exercise Performance", 21 pages.

Office Action for U.S. Appl. No. 14/588,361, mailed on Aug. 17, 2015, Sunil Koduri, "Cloud-Based Initiation of Customized Exercise Routine", 8 pages.

Bauknecht, "We test it—The New Precor Adaptive Motion Trainer", Northwest Runner, Oct. 2013, pp. 14-15.

Mulrooney, "How to Use My Polar Heart Rate Monitor With Life Fitness Equipment", retrieved from <<http://www.livestrong.com/article/223981-how-to-use-my-polar-heart-rate-monitor-with-life-fitness-equipment/>>, Sep. 2, 2010, 7 pages.

Octane Fitness, "Pro4700 Operations Manual", retrieved on Oct. 21, 2013 from <<http://www.octanefitness.com/files/octane/filemgmt/files/pro4700-operations-manual-.pdf>>, 24 pages.

Ursu, "10-Step Guide: How to Use the Weigh Loss Preset Treadmill Workouts", retrieved on Dec. 19, 2013 from <<http://www.performbetter.com/webapp/wcs/stores/servlet/PBOnePieceView?storeId=10151&pagename=283>>, 3 pages.

Waters, "Benefits of Training With Heart Rate Control", retreieved on Dec. 19, 2013 from <<www.smoothfitness.com/fitness-center/articles/training-with-heart-rate-control.htm>>, Smooth Fitness, 2 pages.

PCT Search Report and Written Opinion for Application No. PCT/US2014/072857, mailed Apr. 24, 2015, 9 pages.

PCT Search Report and Written Opinion for Application No. PCT/US14/72854, mailed May 11, 2015, 15 Pages.

PCT Search Report and Written Opinion for Application No. PCT/US2014/072849, mailed Apr. 24, 2015, 12 pages.

Shu, et al., "In-Shoe Plantar Pressure Measurement and Analysis System Based on Fabric Pressure Sensing Array", retrieved from <<http://repository.lib.polyu.edu.hk/jspui/bitstream/1 0397/2527/1/05378500.pdf>>, IEEE Transactions on Information Technology in Biomedicine, vol. 14, No. 3, May 2010, 9 pages.

* cited by examiner

FUZZY LOGIC-BASED EVALUATION AND FEEDBACK OF EXERCISE PERFORMANCE

CROSS REFERENCE TO RELATED APPLICATIONS

This application is based on and claims priority to U.S. Provisional Application No. 61/927,399, filed on Jan. 14, 2014, entitled, "FUZZY LOGIC-BASED EVALUATION AND FEEDBACK OF EXERCISE PERFORMANCE," the contents of which are herein incorporated by reference.

BACKGROUND

Exercise is necessary to maintain both physical and mental health. Although many people prefer exercising outdoors, it is often difficult to do so due to potentially adverse weather conditions and/or unsuitable urban environments. Accordingly, many individuals have taken to exercising indoors in places such as at health clubs, gyms, or even their own home (e.g., a room or garage) where environmental conditions are controllable and predictable. In these settings, weight lifting equipment may be used to improve one's muscular strength, while fitness machines (e.g., treadmills, elliptical machines, stationary bicycles, etc.) may be used for cardiovascular exercise.

Despite the advantages provided by fitness machines, today's fitness machines are limited in what they can do for a user. For example, fitness machines are predominantly "manual" in design. Namely, each time a user begins a workout on a fitness machine, he/she typically provides input data (e.g., weight, age, etc.), and selects a workout program or routine from multiple available routines (e.g., steady pace, interval training, hills, etc.). The available workout routines are often poorly tailored to the specific user of the fitness machine, making it more difficult for users to achieve fitness-related goals given the limited, manual input available on the fitness machine.

Current fitness machines are further limited in the feedback they can provide to the user. That is, any performance-related feedback provided by the fitness machine is generally limited to basic vital information (e.g., heart rate information) of the user. In such a scenario, a user is left to decide for themselves whether he/she should adjust the intensity (e.g., resistance, speed, etc.) of the workout program in an effort to achieve a target heart rate. Moreover, sensing mechanisms are limited to metal handgrips and heart monitoring chest straps configured to measure heart rate and other limited health measurements.

Furthermore, using fitness machines can also be rather boring and monotonous due to the unchanging scenery of most indoor environments. To cure this boredom, users typically listen to music or watch video media while exercising on a fitness machine. However, the novelty of such passive media can eventually wear off, leading to continued boredom while exercising on a fitness machine.

SUMMARY

Described herein are techniques and systems using fuzzy logic methodology for evaluating exercise performance of a user and adjusting intensity of a fitness system, such as a fitness machine or device. One or more intelligent sensors, including at least one camera-based sensor that detects image data of the user, gather data that is provided to a fuzzy system that evaluates the exercise performance. The integration of one or more intelligent sensors with the fitness system transforms the fitness system into a "smart" fitness system that is able to collect image data and other inputs about a user in order to evaluate the user's exercise performance in real-time, and to provide constructive feedback regarding the user's exercise performance. The fitness system described herein may obtain fitness information in a fitness knowledge store that is utilized with fuzzy logic to enable numerous applications, including, but not limited to, evaluation of a user's exercise performance and automatic control of a fitness system to attain and maintain optimal results.

In some embodiments, a fitness system includes a stationary exercise device, and at least one camera-based sensor mounted on the stationary exercise device, the camera-based sensor being configured to detect image data of a user on the fitness system. The fitness system may further include one or more sensors mounted on the stationary exercise device, the one or more sensors being configured to detect information about the user including one or more of body weight, heart rate, blood pressure, oxygen level, hydration level, body temperature, blood glucose level, or respiratory rate, just to name a few examples. The fitness system further includes a fuzzy system to determine an exercise performance condition of the user based, at least in part, on the detected image data and the detected information about the user, and to generate an evaluation of the exercise performance condition or an instruction to take corrective action.

The smart fitness system of the embodiments disclosed herein leverages one or more intelligent sensors, fitness information, and fuzzy logic technology to enable automation of many of the manual processes plaguing current fitness machines, and prescribe workout regimens for any exercise environment that are tailored to specific users' information and goals. During exercise routines, real-time, constructive feedback may be provided to the users based on sensed data, including image data, about the user. In this manner, the fitness system becomes something of a "virtual coach" to the user to help make exercising safer, more interactive, and fun. Moreover, the fitness system may help achieve results and goals of the user faster.

This Summary is provided to introduce a selection of concepts in a simplified form that is further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

The detailed description is described with reference to the accompanying figures. In the figures, the left-most digit(s) of a reference number identifies the figure in which the reference number first appears. The same reference numbers in different figures indicates similar or identical items.

DETAILED DESCRIPTION

Figure 1:
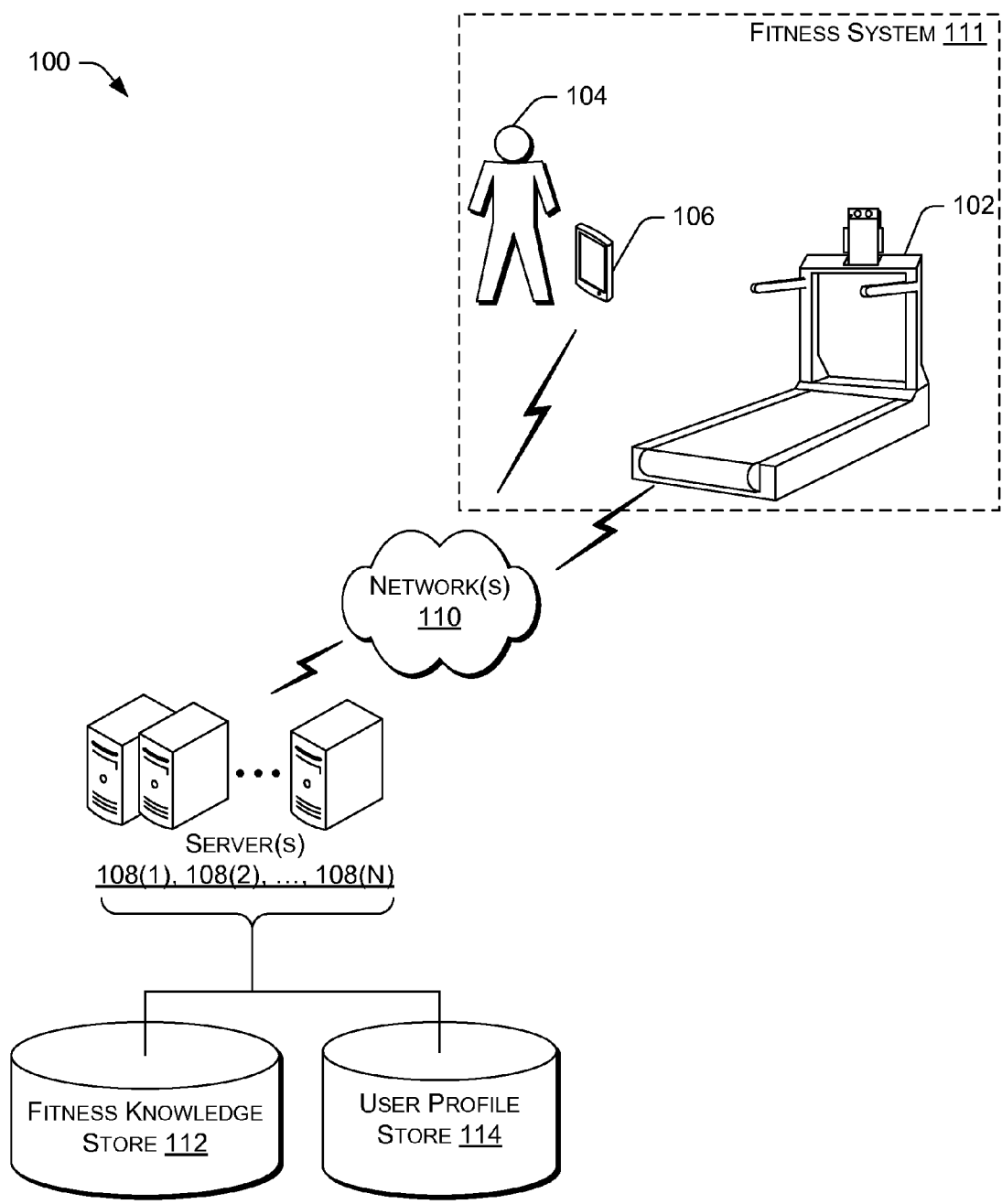
FIG. 1 illustrates an example environment of a cloud-based system (or platform) for implementing a user-customized fitness experience.

Embodiments of the present disclosure are directed to, among other things, techniques and systems for evaluating exercise performance of a user of a fitness system by utilizing fuzzy logic technology, personal data about the user, and real-time exercise performance data measured by one or more sensors. Using such techniques and systems, the fitness system (e.g., a fitness machine) can provide intelligent and personalized feedback to the user. Moreover, the fitness system can be customized not only for each individual user, but also each exercise session of each user.

A fitness system that operates using fuzzy logic technology can perform a variety of functions involving a relatively large number of inputs. Such functions can include generating an exercise performance evaluation for a user, providing real time feedback and guidance to the user, and modifying operating characteristics of the fitness system (e.g., changing the speed or inclination of a treadmill, changing exercise duration of a current session, and so on), just to name a few examples. Such functions can be based on any of a number of the relatively large number of inputs, such as personal data of the user, real-time exercise parameters of a current exercise session, and/or archived exercise parameters of past exercise sessions. A fuzzy system operating on these inputs allows a fitness system (e.g., a fitness machine) to provide intelligent and personalized feedback to the user. Some of these inputs may be relevant only for some particular conditions and may be considered only when these particular conditions exist. In this way, for example, processing overhead can be relatively low compared to the case where processing a full gamut of input parameters is always performed regardless of the existing conditions. Further, the operating structure of a fuzzy system uses a rule-based structure that is relatively simple, involving efficient coding and system documentation, compared to systems that are based on the use of traditional technologies.

A fuzzy system operates using fuzzy variables that take fuzzy sets as their values. A fuzzy set is characterized by a membership function defined on "the universe of discourse". The universe of discourse is the space where the fuzzy variables are defined. The membership function gives the grade, or degree, of membership in a fuzzy set to all the elements of the universe of discourse. For classic fuzzy sets, the membership function maps the elements of the universe of discourse onto numerical values in the interval [0, 1]. A membership function value of zero implies that the corresponding element is definitely not an element of the fuzzy set, while a value of one implies that the corresponding element fully belongs to the fuzzy set. Partial belonging of an element in a fuzzy set is implied if the corresponding grade lies between zero and one. For example, the height of a user may be considered by a fitness system to determine correct posture of the user during an exercise session. Without involving fuzzy sets, if the user is taller than a particular threshold then the user belongs to the "set of tall people", otherwise the user belongs to the "set of short people". However, such a sharp change of state across the particular threshold can lead to inaccurate or undesirable outcomes. Thus, in more realistic situations there tends to be a natural "fuzzification" where a smooth membership curve better describes the grade (e.g., the height of the user) for which an element belongs to a set. Fuzzification is a process of decomposing a system input and/or output into one or more fuzzy sets. Any input can be interpreted from a fuzzy set and a grade can be determined from associated membership function. The membership functions overlap to allow smooth mapping of the system and to add to system robustness. The process of fuzzification allows the system inputs and outputs to be expressed in a substantially continuous set of terms so that rules can be applied in a simple manner to express a complex system.

Although embodiments disclosed herein are often described with reference to a treadmill, other types of stationary exercise devices can be used with the techniques and systems disclosed herein without changing basic characteristics of the system. Such other types of stationary exercise devices that may make up part of the fitness system disclosed herein include, but are not limited to, elliptical machines, stationary bicycles, rowing machines, stair climbers, exercise pools (i.e., swimming machines), weight machines, and similar types of devices. Moreover, embodiments disclosed herein may comprise fitness machines built for cardiovascular exercise, strength exercise (e.g., weight machines), and/or flexibility exercise, just to name a few examples. The disclosed fitness system may be implemented and used in various environments and settings, including, but not limited to, health clubs or gyms, medical rehabilitation centers, corporate offices, household fitness environments, outdoor environments, and the like. For example, in some embodiments, fitness systems or machines may be implemented in any suitable environment, such as a living room or other similar household environment, an outdoor environment, and so on.

The embodiments disclosed herein pertain to a fitness system using a fuzzy system and one or more sensors to determine and evaluate an exercise performance condition of a user. An "exercise performance condition," as used herein, may relate to any suitable user performance metric, such as body form, stance, exercise pace, stride length, and/or vital information (e.g., heart rate, hydration level, etc.) that may provide a basis for determining how well the user is performing with respect to referenced fitness information. In some embodiments, user interface aspects of the system may be in the form of a virtual assistant or virtual persona that assists the user with his/her workout regimen.

The techniques and systems described herein may be implemented in a number of ways. Example implementations are provided below with reference to the following figures.

Example Environment

FIG. 1 illustrates an example environment of a cloud-based system 100 including, among other things, a fitness machine 102 (sometimes referred to herein as a "smart fitness machine 102"). In the cloud-based system 100, a user(s) 104 is associated with the fitness machine 102 at any given time, such as when the user 104 decides to exercise on the fitness machine 102.

The user 104 may also be associated with a client computing device(s) ("client device") 106 that is configured to communicate via wired or wireless communication with the fitness machine 102, and further to access, or cause the fitness machine 102 to access, one or more servers 108(1), 108(2), . . . , 108(N) via a network(s) 110. For example, the client device 106 may be physically connected to the fitness machine 102 through electrical couplings such as wires, pins, connectors, etc., to utilize a wired communication protocol (e.g., universal serial bus (USB)), or the client device 106 may be wirelessly connected to the fitness machine 102, such as via WiFi protocol, a short-wave radio frequency (e.g., Bluetooth®), or another suitable wireless communication protocol. The client device 106 may further utilize a communication interface to access the server(s) 108(1)-(N) via the network 110. The user 104 may represent various different types of users, such as a user 104 interested in casual fitness, recreational fitness, or a competitive or professional athlete. Such different types of users are discussed in more detail below with reference to user profiles.

In other embodiments, techniques and systems described herein may be implemented sans cloud networking and absent network 110 and server(s) 108(1)-(N). For example, fitness machine 102 and client device 106 may comprise a system that is sufficient to perform techniques for evaluating exercise performance of user 104 on fitness machine 102 by using fuzzy logic methodology. Further, communication between fitness machine 102 and client device 106 may be performed wired and/or wirelessly, and claimed subject matter is not limited in these respects.

The client device 106 and/or the fitness machine 102, and/or certain components of the fitness machine 102 may constitute a networked fitness system 111. The networked fitness system 111 (or any individual device thereof), either automatically or at the direction of the user 104, may access the server(s) 108(1)-(N) via the network 110 to obtain or upload various types of data, and the networked fitness system 111 may also receive messages such as email, short message service (SMS) text messages, messages via an application associated with the client device 106 or the fitness machine 102, and the like, via the network 110. In this sense, the networked fitness system 111 and the server(s) 108(1)-(N) constitute a distributed platform (i.e., a combination of software and hardware components) that provides a complete fitness experience for users (e.g., the user 104) of the platform, and where users can experience a customized fitness program that is tailored to the particular user.

The client device 106 may be implemented as any number of computing devices, including a personal computer, a laptop computer, a tablet computer, a portable digital assistant (PDA), a mobile (smart) phone, fitness trackers (e.g., a Nike® FuelBand®, FitBit® activity trackers or wristbands, etc.), a thumb drive, a key fob, a portable media player, a portable game player, a smart watch, and so forth. The client device 106 and the fitness machine 102 are each equipped with one or more processors and memory to store applications and data. The client device may include a fuzzy system that may be part of the one or more processors and/or may be code stored in the memory and executable by the one or more processors.

According to some embodiments, a browser application is stored in the respective memories of the client device 106 and the fitness machine 102 and executes on the respective processors to provide access to the server(s) 108(1)-(N). The browser may render web pages served by a site operated by the server(s) 108(1)-(N) on an associated display of the client device 106 and/or the fitness machine 102. Although embodiments are described in the context of a web based system, other types of client/server-based communications and associated application logic could be used in the cloud-based system 100. The network 110 is representative of many different types of networks, such as cable networks, the Internet, local area networks, mobile telephone networks, wide area networks and wireless networks, or a combination of such networks.

The server(s) 108(1)-(N) may be maintained and operated by an entity such as a service provider associated with the fitness machine 102. For example, a service that facilitates cloud-based storage and management of fitness data for users may maintain the server(s) 108(1)-(N) to provide various fitness services to the user 104. For example, the servers(s) 108(1)-(N) may handle requests, such as in the form of a uniform resource locator (URL), from the fitness machine 102 and/or the client device 106, and serve, in response, various information and data, such as in the form of a web page, to the fitness machine 102 and/or the client device 106, allowing the user 104 to interact with the data provided by the server(s) 108(1)-(N). In this manner, an entity maintaining the server(s) 108(1)-(N) is representative of essentially any service provider supporting user interaction with fitness-related data, including health club sites, equipment maker sites, social networking sites, etc.

In some embodiments, the server(s) 108(1)-(N) have access to a fitness knowledge store 112 that is a repository of fitness knowledge information, such as how to walk, run, stretch, bike, row, etc. with proper body form. In particular embodiments, the client device 106 includes memory storing information equivalent to that stored in the fitness knowledge store 112. The fitness knowledge store 112 may also contain information pertaining to preferable levels, and/or ranges, of body mass index (BMI), heart rate, hydration, blood pressure, blood glucose, respiratory rate, temperature, and the like that may be mapped across various activity levels (e.g., moderate vs. intense exercise) and/or demographic information that may include age, gender, race or ethnicity. For instance, health and fitness experts (e.g., sports medicine experts) and other resources may be utilized to populate the fitness knowledge store 112 with information on recommended exercise regimens, including frequency, intensity, and duration of workouts recommended across various user profile types. Such a fitness knowledge store 112 may be leveraged for customization of exercise routines and for providing constructive feedback to specific individuals that is based on known information about the individuals.

In some embodiments, the server(s) 108(1)-(N) also have access to a user profile store 114 that stores information on multiple users, including the user 104 of FIG. 1. In particular embodiments, the client device 106 includes memory storing information equivalent to that stored in the user profile store 114. The user profile store 114 maintains profiles for individual users based on collected information about the user. The user profiles may be associated with the user information including, but not limited to, a username and password, name of the user, mailing address, phone number, electronic mail (e-mail) address, social media accounts and profiles (e.g., Facebook®, Twitter®, etc.), gender (e.g., male or female), date of birth (i.e., age), race or ethnicity, height, weight, health conditions (e.g., heart disease, cancer, previous strokes, respiratory disease, injuries, diabetes, Alzheimer's disease, depression, liver disease, kidney disease, blood pressure, etc.), and so on.

The user 104 may provide fitness goals or objectives as part of an initial profile setup to be stored in the user profile store 114. For example, categories such as "lose weight", "stay fit", "improve endurance", "train for race", or "recover from injury (rehabilitation)" are examples of options that may be provided to a user 104 for selection of a fitness goal. In some embodiments, specific events (e.g., the Boston Marathon) may be specified by the user 104 as a specific goal for training purposes. In this scenario, the fitness machine 102 may be configured to present a virtual course of the specific event during the exercise routine so that the user 104 can simulate the event for training purposes.

In some embodiments, the user 104 may access a site on the server(s) 108(1)-(N) to answer a questionnaire that facilitates automated selection, by the server(s) 108(1)-(N), of a fitness goal. In some embodiments, the user profile store 114 further maintains schedule information for the user 104, such as a schedule that indicates dates and times of upcoming exercise routines according to a prescribed exercise regimen. This schedule may consider an availability of the user 104 based on a personal calendar of the user 104. As such, an exercise regimen may be catered to a user 104 depending on their availability. For example, a full-time worker may only have an hour or two each day available for exercise, while a professional athlete who is devoted to training full time may be available to exercise much more frequently (e.g., multiple times throughout a single day and for extended duration).

In some embodiments, users that setup profiles in the user profile store 114 may be categorized according to profile types. This categorization may be based on explicit selection by the user 104, or alternatively, the server(s) 108(1)-(N) may be configured to determine a categorization for users based on information provided by the users, or based on answers to predetermined questions. An illustrative example of possible categories for profile types are: (1) Casual Fitness; (2) Recreational; (3) Competitive; and (4) Physical Therapy. Attributes of the "Casual Fitness" profile type may be users that: would like to lose weight or get in shape, are not serious about running, may be fine with just walking for exercise, are not consistent with an exercise regimen, are unsure about technology, may have medical issues, are not receptive to online training, and are not motivated to train or adjust. Attributes of the "Recreational" profile type may be users that: are casual runners, may be interested in running, may be interested in exercising, are fairly regular with an exercise regimen, are receptive to technology, exercise to aid medical issues, utilize online training, and are easier to train and adjust. Attributes of the "Competitive" profile type may be users that: are active runners, enjoy running, are excited about competing, are consistent in a daily exercise regimen, are very selective in technology, have minimal health issues, seek professional training, and are harder to teach. Attributes of the "Physical Therapy" profile type may be users that: have suffered a physical injury and are using exercise as physical therapy in an effort to rehabilitate and get healthy.

At least some of the information maintained in the user profile store 114 may be received from explicit user input via a user interface of either or both of the client device 106 or the fitness machine 102, while some of the information may include implicit information received via sensors of the fitness machine 102 (e.g., heart rate, weight for BMI calculation, body temperature, etc.), or from other sources, such as other fitness related products that track workout history information (e.g., Nike® FuelBand, Fitbit® trackers and wristbands, etc.). With more information obtained from the user 104, a more complete a user profile may be created and stored in the user profile store 114 for use by the fitness machine 102.

Example System Implementation

Figure 2:
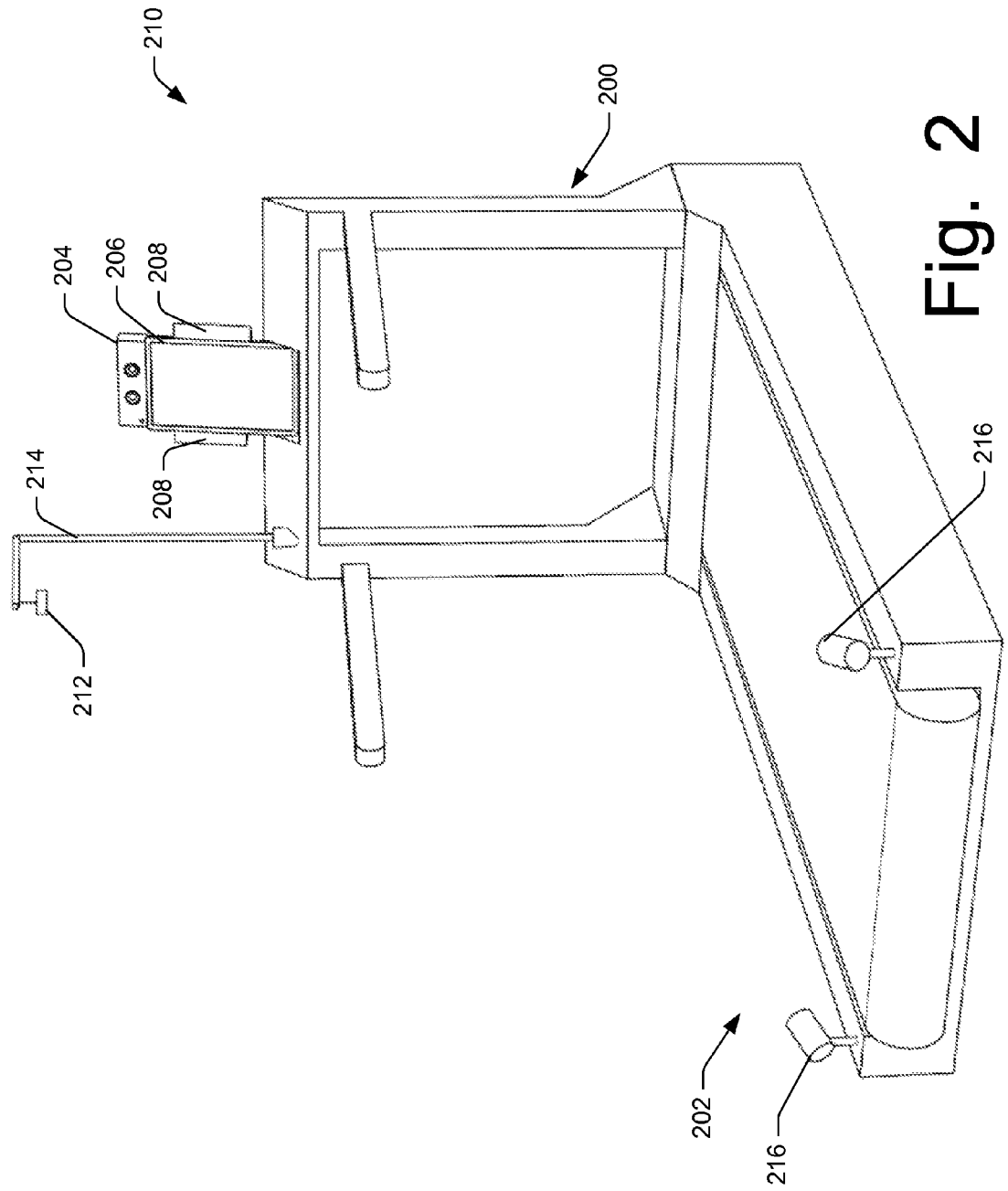
FIG. 2 illustrates a perspective view of an example fitness system according to an embodiment including a camera-based sensor mounted on a fitness machine, and multiple additional sensors for detecting user information about a user of the fitness system.

FIG. 2 illustrates a perspective view of the example fitness machine 102 of FIG. 1 as one suitable implementation environment for the systems and techniques disclosed herein. FIG. 2 shows a stationary exercise device of the fitness machine 102 in the form of a treadmill. However, it is to be appreciated that the fitness machine 102 may comprise any suitable stationary exercise device (e.g., a stationary bike, an elliptical machine, a rowing machine, a stair climber, a swimming machine, etc.) without changing the basic characteristics of the system. The fitness machine 102 may comprise a front end 200 and a back end 202. A camera-based sensor 204 may be mounted at any suitable location on the fitness machine 102 and communicatively coupled to the fitness machine 102 via wired or wireless connection. In some embodiments, the camera-based sensor 204 is mounted at the front end 200 of the fitness machine 102, such as above a display 206 that may also be mounted at the front end 200. In general, the display 206 may be located in the line of site of the user 104, while the camera-based sensor 204 may be mounted at any suitable location on, or around, the fitness machine 200. Mounting the camera-based sensor 204 at the front end 200 of the fitness machine 102 allows the camera-based sensor 204 to obtain image data of the user 104 from the front side of the user's body. In some embodiments, the camera-based sensor 204 may be able to detect objects from as close as approximately 2 feet from the camera-based sensor 204 and as far as approximately 14 feet from the camera-based sensor 204. The camera-based sensor 204 may further comprise a viewing angle of approximately 70 degrees.

In some embodiments, the camera-based sensor 204 may be part of the networked fitness system 111 without the fitness machine 102. In such environments, the camera-based sensor 204 may be implemented in a living room, or on other recreational and/or fitness equipment (e.g., a bicycle, rowing boat, etc.), and the camera-based sensor 204 may be mountable to a variety of types of structures to be implemented in those environments. For example, the camera-based sensor 204 may comprise a substantially flat base for setting or mounting the camera-based sensor 204 on a flat surface (e.g., a television display stand, the top of a display, etc.), with or without fasteners (e.g., screws, bolts, etc.) or other type of adhesive or mounting component (e.g., hook-and-loop or Velcro-type fastening elements, etc.). In some embodiments, a mounting structure for the camera-based sensor 204 may include a clip (e.g., spring-loaded clip), ball-and-socket mounting component, or a similar mounting structure that facilitates easy mounting and dismounting of the camera-based sensor 204 onto, or off of, a structure.

The camera-based sensor 204 may comprise a capture device in the form of a depth camera configured to visually monitor the user 104 by collecting image data of the user 104. One suitable example device that may be used as the camera-based sensor 204 is the Kinect® sensor used with the Xbox® console system from Microsoft® Corporation of Redmond, Wash. The camera-based sensor 204 may be configured to continuously detect image data (i.e., capture video) of the user 104 with depth information so that movements of the user 104 may be interpreted by onboard processing units of the camera-based sensor 204 and/or computing components of the fitness machine 102, which will be described in more detail below with reference to FIG. 3. The camera-based sensor 204 may use any suitable technique to capture image data with depth information (e.g., time-of-flight (ToF), structured light imaging, stereo imaging, etc.) to facilitate the techniques described herein. Accordingly, the camera-based sensor 204 may include one or more of a depth camera, a video camera (e.g., red-green-blue (RGB) video camera), stereo cameras, and/or other suitable capture devices using charge-coupled device (CCD) sensors, complementary metal-oxide-semiconductor (CMOS) sensors, and/or infrared (IR) sensors. In some embodiments, the camera-based sensor 204 is configured to emit IR light as a means of ToF imaging.

One illustrative scenario in which movements of the user 104 may be captured by the camera-based sensor 204 and interpreted by the components of the fitness machine 102 is when the user 104 is running on a treadmill that makes up the stationary exercise device portion of the fitness machine 102. For example, exercise performance conditions in the form of running movements of the user 104 may be interpreted in order to determine whether the user 104 is exhibiting proper running form. In order to make such a determination, the fitness machine 102 may download in advance, or request in real-time, information contained in the fitness knowledge store 112 pertaining to proper running form. That is, the fitness machine 102 may interpret the movements of the user 104 from the image data collected by the camera-based sensor 204 to determine whether the user 104 is running with proper form by comparing an exercise performance condition derived from the image data to reference data selectively retrieved from the fitness knowledge store 112. In some implementations, reference data is selectively retrieved from the fitness knowledge store 112 based, at least in part, on a fuzzy system operating on, among other things, image data obtained from the camera-based sensor 204. It is to be appreciated that running on a treadmill is but one example scenario of utilizing the camera-based sensor 204 for exercise performance evaluation, and various other types of movements (e.g., walking, stretching, etc.) of the user 104 may be collected by the camera-based sensor 204 and interpreted and utilized for performance evaluation, as will be described in more detail below.

In addition to tracking movements of the user 104 during an exercise routine, the camera-based sensor 204 may be configured for additional uses, such as receiving gestural input commands from the user 104, identifying the user 104 with face recognition techniques, and other similar functions. For example, the server(s) 108(1)-(N) may collect image data of the faces of registered or subscribed users of the cloud-based system 100 of FIG. 1 upon, or after, initial registration with a fitness information service. Accordingly, upon the user 104 positioning themselves in front of the camera-based sensor 204, such as at the beginning of an exercise routine, the fitness machine 102 may recognize the user 104 by identifying the face of the user 104 using the camera-based sensor 204.

In some embodiments, the camera-based sensor 204 may be configured to detect a heart rate of the user 104 by detecting changes in skin tone or with other suitable visual cues. For instance, IR or another suitable radiation may be emitted by the camera-based sensor 204 toward the user 104, and an image sensor in the camera-based sensor 204 may detect light that is reflected, and deduce from light that is not reflected that that the non-reflected light has been blocked by blood pulsating through a blood vessel of the user 104. Accordingly, light signals detected at pulsed measurements may correspond to blood flow measurements so that heart rate can be deduced from the light signals detected at the camera-based sensor 204. The camera-based sensor 204 may further be configured to detect facial expressions to interpret emotional states (e.g., happy, worried, sad, etc.) of the user 104. The camera-based sensor 204 may further be configured to detect muscle tension of the user 104 for various muscle groups (e.g., neck, shoulders, hands, etc.) based on suitable visual cues, such a by a flex angle of limbs.

The display 206 of the fitness machine 102 may be any type of display, such as a liquid crystal display (LCD), plasma, electrophoretic, or any other suitable display type. The display 206 may be touch-enabled to allow control by the user 104 of user interface (UI) elements presented on the display 206 using touch, or proximity-based, input. For example, the user 104 may use one or more fingers to provide use single or multi-touch gestural input to the display 206 via a UI presented on the display 206. Touch-enabled displays suitable for use as the display 206 may be based on any suitable touch-based technology, including, but not limited to, capacitive, resistive, surface acoustic wave (SAW), infrared, optical, or any other suitable touch-based technology. In some embodiments, the display 206 may be mounted in a manner to allow the display 206 to swivel vertically and/or horizontally, enabling the user 104 to manipulate the orientation of the display 206 to their liking.

In some embodiments, the fitness machine 102 may further include one or more speakers 208 mounted at the front end 200 of the fitness machine 102 to provide audio output to the user 104. Such audio output may comprise music and/or speech synthesized output of the fitness machine 102 to provide performance-based feedback to the user 204, instructions to take corrective action, or general audio output to the user 204 (e.g., sounds, alarms, etc.). An earphone/ear bud jack or plug may further be provided on the fitness machine 102 to allow the user 104 to use ear buds for audio output.

The fitness machine 102 may include other computing system components to enable the various techniques and processes described herein. Such components may be housed within the enclosure of the display 206, or within another suitable compartment of the fitness machine 102. Example computing system component will be described in further detail with reference to FIG. 3, below.

In some embodiments, additional sensors may include a substantially noninvasive scanning device 212, such as a medical tricorder, configured to take health measurements (vital information) including, but not limited to, heart rate, blood pressure, body temperature, oximetry (blood oxygenation), hydration, heart rate variability (HRV), pulse wave transit time (PWTT) (i.e., a measure of the time it takes for a beat from the user's heart to reach somewhere else in the user's body), and the like. The scanning device 212 may be further configured to run an electrocardiogram (EKG), detect stress levels, and so forth.

In some implementations, processing operations involving fuzzy logic methodology may be applied to data measured by the camera-based sensor 204 and/or the scanning device 212 to provide an exercise performance evaluation for the user. For example, the user's personal data (e.g., age, health condition, etc.), posture, and real-time heart rate may be used as input variables for a fuzzy system that generates an evaluation of exercise performance by the user or instructions for the user to take corrective action against real-time exercise errors (e.g., incorrect posture for the user's age group, overly aggressive workout for the user's current physical condition, and so on).

The scanning device 212 may be mounted at the front end 200 of the fitness machine 210, such as proximate the display 206 and upon a portion of the fitness machine 210 structure. One example mounting structure 214 is shown in FIG. 2 comprising a stand and retractable cord arrangement so that the user 104 does not have to worry about dropping the scanning device 212 onto the floor, which could potentially damage the scanning device 212. In some embodiments, the scanning device 212 may receive vital information about the user 104 in a noninvasive manner, such as by optical-based detection without the need for user intervention.

In other embodiments, the user 104 may grasp the scanning device 212 at any time while on the fitness machine 210, such as before, during, or after exercising on the fitness machine 210, and use the scanning device 212 to collect vital information about the user 104 in a substantially noninvasive manner. For example, the user 104 may pull the scanning device 212 toward them, extending the retractable cord of the mounting structure 214, and contacts their forehead with the scanning device 212 in order to measure vital information. In some embodiments, the scanning device 212 may be included as part of a wearable device, such as a smart watch or fitness band to be worn by the user 104. At least a substantially noninvasive technique for taking vital measurements is suitable for use on the fitness machine 210, leaving the user 104 substantially uninterrupted during an exercise routine. It is to be appreciated that the mounting structure 214 is but one example mounting mechanism that may be used with the fitness machine 210, and the scanning device 212 may be mounted on the fitness machine in any suitable manner, such as by inserting the scanning device into a slot or compartment on the fitness machine 210, and so forth.

The fitness machine 210 may further include one or more additional cameras 216 mounted at the back end 202 of the fitness machine 210. The cameras 216 may comprise depth cameras to enable observation of user movements from vantage points that the camera-based sensor 204 may not be able to view (e.g., the entire profile of the user 104). In some embodiments, the cameras 216 may comprise IR-based cameras that are configured to sense IR light for imaging purposes. In some embodiments, the cameras 216 are configured to detect image data of the user 104 which may be processed by downstream components of the fitness machine 210 by utilizing image stitching software to compose a three-dimensional (3D) model of the user 104 based on separate two-dimensional (2D) images obtained from each of the cameras 216. Accordingly, it is to be appreciated that any number of cameras 216 may be utilized with the fitness machine 210, and two cameras 216 are shown merely as an example number of cameras 216 in FIG. 2B that is suitable for the purposes of the embodiments disclosed herein.

More or fewer sensors than those depicted in FIG. 2 may be utilized without changing the basic characteristics of the system. In general, the camera-based sensor 204 and the additional sensors 212 and 216 of the fitness machines 102, 210 are substantially noninvasive in that they do not require blood samples, urine, or anything that may substantially interrupt the user 104 during an exercise routine. In some embodiments, the fitness machine 210 may include additional sensors configured to obtain respiratory rate, blood glucose (e.g., by taking sweat samples of the user 104), and the like. The scanning device 212 and cameras 216 may be communicatively coupled to the fitness machine 210 via wired or wireless (e.g., Bluetooth®) connection in order to transmit collected information about the user 104 to the fitness machine 210 where it may be analyzed and interpreted for various applications.

In some embodiments, the fitness machine 102, 210 may be further configured to receive and process data from external sensors that are provided by the user 104. For example, a user-provided sensor may be in the form of an electronic textile (e-textile) sensor configured to detect pressure forces on a foot of the user 104 while the user 104 is exercising on the fitness machine 102, 210. A garment of the user 104, such as a sock, may be embedded, or filled, with an e-textile sensor material configured to detect pressure distribution on the foot of the user 104 when walking, running, stretching, and the like. An anklet may be magnetically coupled to corresponding magnetic elements embedded in, or attached to, the sock. The anklet may be configured to receive data from the e-textile sensor material in the sock, and communicate the collected data wirelessly to the fitness machine 102, 210. An example product suitable for use as the e-textile sensor is the Sensoria® sock with a Bluetooth®-enabled anklet. In addition to pressure data, the e-textile sensor may be configured to register and count discrete steps by the user 104 to enable stride cadence and other useful measurements that may be analyzed to determine exercise performance conditions of the user 104.

In some implementations, processing operations involving fuzzy logic methodology may be applied to data measured by the e-textile sensor to provide an exercise performance evaluation for the user. For example, the e-textile sensor can detect pressure forces on a foot of the user 104 while the user 104 is exercising over a period of time, such as ten minutes, twenty minutes, an hour, and so on. Records of such pressure forces for a particular user performing a number of exercise sessions can be archived and compared with measured pressure forces for a current exercise session. The user's personal data (e.g., casual exerciser or marathon trainer, etc.), archived pressure force data, and current pressure force data may be used as input variables for a fuzzy logic control system that generates an evaluation of exercise performance by the user or instructions for the user to take corrective action against real-time exercise errors (e.g., subtle posture imbalance, severe posture imbalance, and so on). Such an evaluation of exercise performance being based on exercise history of the user can reveal exercise habits that may be very bad, slightly bad, ignorable, slightly good, or very good, depending on intent of the user. For example, a user training for a long-distance marathon does not want to tolerate even subtle posture imbalances, and would like to be notified of such an exercise practice. On the other hand, a casual-exercise user may not wish to be bothered by notifications of subtle posture imbalances, and would only like to be notified if the posture imbalances are severe.

Figure 3:
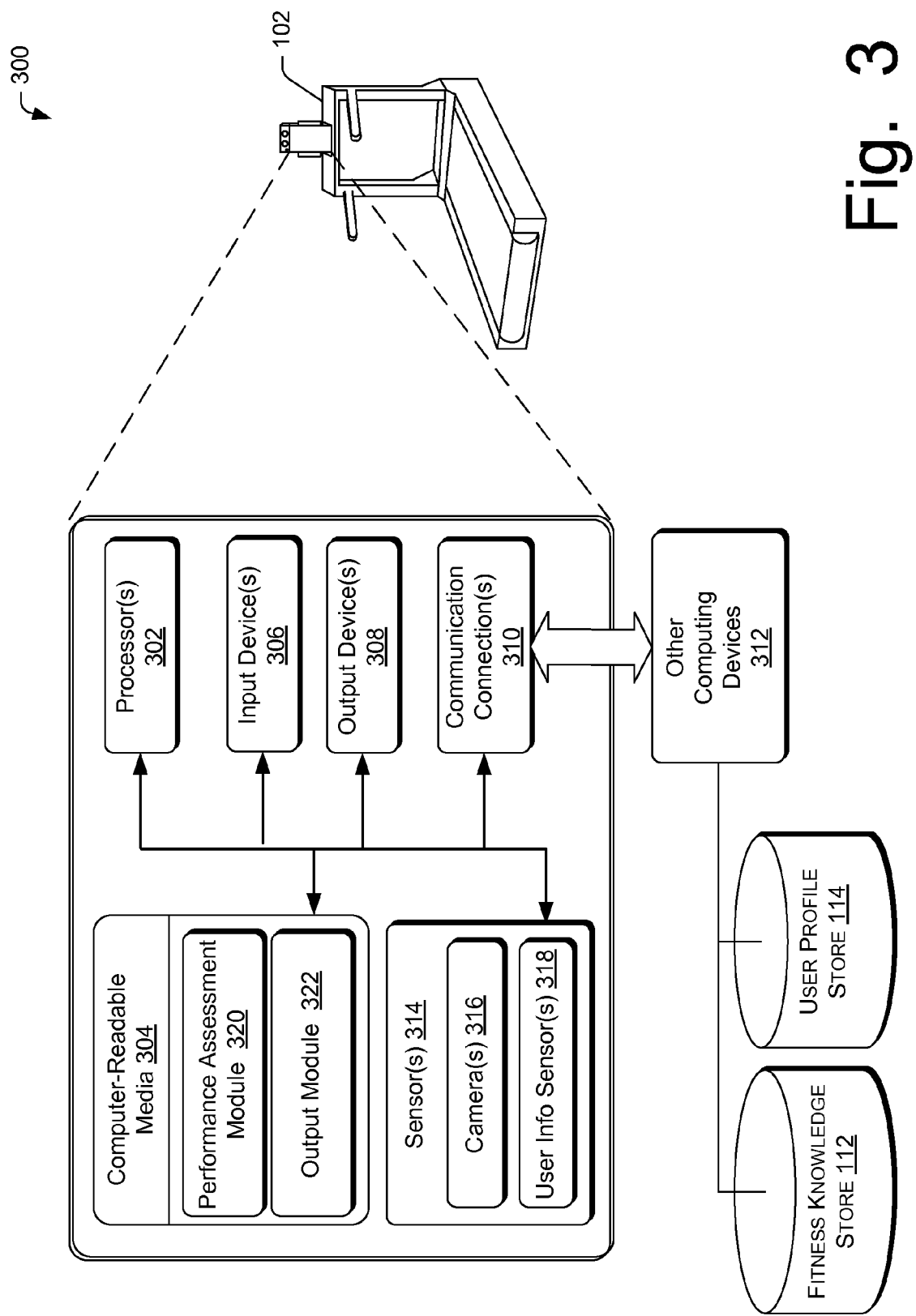
FIG. 3 is a block diagram of an example computing environment of an example fitness system, including various components of the fitness system, according to some embodiments.

FIG. 3 is a block diagram of an example computing environment 300 including an example fitness system, such as the fitness machine 102 of FIG. 1. The computing environment 300 shown in FIG. 3 is only one illustrative example of a computing environment and is not intended to suggest any limitation as to the scope of use or functionality of the computing environment 300. Neither should the computing environment 300 be interpreted as having any dependency nor requirement relating to any one or combination of components illustrated in FIG. 3.

In at least one configuration, the fitness machine 102 comprises one or more processors 302 and computer-readable media 304. The fitness machine 102 may also include additional data storage devices (removable and/or non-removable) such as, for example, magnetic disks, optical disks, or tape. Such additional storage may include removable storage and/or non-removable storage. Computer-readable media 304 may include, at least, two types of computer-readable media 304, namely computer storage media and communication media. Computer storage media may include volatile and non-volatile, removable, and non-removable media implemented in any method or technology for storage of information, such as computer readable instructions, data structures, program modules, or other data. The system memory, the removable storage and the non-removable storage are all examples of computer storage media. Computer storage media includes, but is not limited to, random access memory (RAM), read-only memory (ROM), erasable programmable read-only memory (EEPROM), flash memory or other memory technology, compact disc read-only memory (CD-ROM), digital versatile disks (DVD), or other optical storage, magnetic cassettes, magnetic tape, magnetic disk storage or other magnetic storage devices, or any other non-transmission medium that may be used to store the desired information and which may be accessed by the fitness machine 102. Any such computer storage media may be part of the fitness machine 102. Moreover, the computer-readable media 304 may include computer-executable instructions that, when executed by the processor(s) 302, perform various functions and/or operations described herein.

In contrast, communication media may embody computer-readable instructions, data structures, program modules, or other data in a modulated data signal, such as a carrier wave, or other transmission mechanism. As defined herein, computer storage media does not include communication media.

The processor(s) 302 and computer-readable media 304 may be housed within the enclosure of the display 206 shown in FIG. 2, or the processor(s) 302 and computer-readable media 304 may be located at any other suitable position within the fitness machine 102 structure. The fitness machine 102 may include one or more input devices 306, such as the touch screen display 206, physical buttons (e.g., keyboard or keypad) on the display 206 and/or the fitness machine 102, the camera-based sensor 204 of FIG. 2 configured to receive gestural input from the user 104, a microphone or microphone array for receiving voice input commands from the user 104, pointing devices (e.g., mouse, pen, stylus, etc.), remote controls, or any other suitable input device for interfacing with the fitness machine 102.

The fitness machine 102 may include one or more output devices 308 such as the display 206, the speakers 208, or any other suitable output device coupled communicatively to the processor(s) 302 and the computer-readable media 304. The output devices 308 may serve the purpose of providing output to the user 104, such as providing fitness related information via the display 206, for example, or providing an evaluation of the user's exercise performance and/or an instruction for the user 104 to take corrective action during an exercise routine. The fitness machine 102 may be configured to provide any suitable visual data via the display 206 to the user, such as cable television content, streamed video, image or text data, such as from the server(s) 108(1)-(N). The display 206 may further be configured to enter a "sleep" state after a predetermined time has passed with no input to the fitness machine 102.

The fitness machine 102 may further contain communications connection(s) 310 that allow the fitness machine 102 to communicate with other computing devices 312 such as via a network. The other computing devices 312 may include the client device 106 and the server(s) 108(1)-(N), among other computing devices 312. Accordingly, the communications connection(s) 310 may facilitate communication over the network(s) 110 to enable the fitness machine 102 to access the fitness knowledge store 112 and/or the user profile store 114. Additionally, the communications connection(s) 310 may enable WiFi-based communication such as via frequencies defined by the IEEE 802.11 standards, short range wireless frequencies such as Bluetooth®, or any suitable wired or wireless communications protocol that enables the fitness machine 102 to interface with the other computing devices 312 in relatively close proximity to the fitness machine 102.

The fitness machine 102 may further include one or more sensors 314, such as one or more camera-based sensors 316 to detect image data of a user on the fitness machine 102. In some embodiments, the one or more camera-based sensors 316 may include the camera-based sensor 204 and possibly the one or more cameras 216 discussed with reference to FIG. 2. The one or more sensors 314 may further include one or more user information sensors 318, such as the scanning device 212 of FIG. 2, configured to noninvasively collect various vital measurements from the user 104. Together, the sensors 314 are configured to collect various types of information about the user 104. For instance, the one or more camera-based sensors 316 are configured to collect image data from the user 104 before, during, and after exercising on the fitness machine 102. The user information sensors 318 may be configured to collect other types of information about the user, such as vital measurements, and similar information that may not be detectable from visual cues alone.

The computer-readable media 304 of the fitness machine 102 may store various modules, including a performance assessment module 320 and an output module 322. The performance assessment module 320 may include fuzzy logic software or other processing software that is configured to process signals received from the sensor(s) 314 and the input device(s) 306 to determine an exercise performance condition of the user 104. For example, the performance assessment module 320 may receive image data collected by the camera-based sensor 316, analyze the image data to determine an exercise performance condition of the user 104 by referencing information obtained from the fitness knowledge store 112, and evaluate the exercise performance condition in terms of how well the user 104 is performing (e.g., ideally, incorrectly, etc.). For example, an exercise performance condition derived from the collected image data may include a condition of the body form of the user 104 (e.g., body lean the left of vertical, etc.). An evaluation of the example exercise performance condition may indicate poor body form, and may be provided to the user 104 as constructive feedback via the output device(s) 308. In some embodiments, the performance assessment module 320 may be configured to process inputs from other external sensors, such as an e-textile sensor described above. The collected data from such an external sensor may be received via the communication connection(s) 310 of the fitness machine 102.

The output module 322 may be configured to output the evaluation of the exercise performance condition made by the performance assessment module 320. Additionally, in cases where the evaluation indicates performance that is anything but ideal, correct, or expected, an instruction to take corrective action (e.g., "keep upper body erect", etc.) may be provided by the output module 322. The output module 322 may cause such information to be output via the output device(s) 308, such as by displaying video, graphics, image, and/or text data via the display 206, and/or providing audio output via the speakers 208 (e.g., audible instructions to take corrective action).

In some embodiments, the output module 322 is configured to generate and display, via the display 206, an avatar of the user 104 based on information about the user 104 in the user profile store 114 and/or data collected from the sensor(s) 314. The avatar provided by the output module 322 may be any graphical representation of the user 104 in two-dimensional or three-dimensional form. In some embodiments, the avatar may loosely resemble the physical appearance of the user 104 and track the user's progress by changing the appearance of the avatar as the user loses (or gains) weight and/or gains (or loses) strength. For example, based on height, weight, gender, and other suitable information obtained about the user 104 from the user 104 and/or the sensors 314, an avatar may be created that is reflective of the user's traits that may be visually depicted by the avatar. The output module 322 may be configured to present current avatars with (e.g., next to) previous avatars of the user 104 that were generated days, weeks, months, or years earlier in order to show progress that the user 104 has made over time in terms of their fitness.

In some embodiments, user interface aspects of the networked fitness system 111 may present as a virtual assistant, such as an operating system agent, that is given a persona (e.g., Zsolutionz™ Optimal Fitness Interactive Experience (ZOFIE™)) so that the user 104 may experience a more personalized or human type of interaction with the platform. Some aspects of the virtual assistant may be downloaded to the client device(s) 106 and/or the fitness machine 102 for access thereon even when a network connection is unavailable. However, information accessible to the virtual assistant may remain "in the cloud" so that the virtual assistant may provide a customized exercise experience to the user 104 from any location where a network connection is available.

It is to be appreciated that some or all of the components and corresponding functionality described herein with reference to FIG. 3 may be provided by one or more computing device, such as the client device 106, which may represent at least part of the networked fitness system 111. For example, sensors 314 embedded in, coupled to, or otherwise associated with the client device 106 may be configured to collect data (e.g., image data) about the user 104 in order for the client device 106 to generate an evaluation of the user based on fuzzy logic. Thus, the networked fitness system 111 may be implemented in virtually any suitable environment, such as outdoors. For instance, the sensors 314 may be mounted at any suitable location (e.g., in a living room of a user's home) and coupled to (e.g., embedded within) a networked client device 106 so that the sensors 314 can collect fitness-related information about the user 104, even when the user 104 is not on a fitness machine 102. In these scenarios, the sensors 314 may be capable of being mounted on a variety of structures in different environments (e.g., flat surface mounting, clips, ball-and-socket mounts, etc.), or otherwise be embedded in a client device 106 that may be carried or worn by the user 104. The more sensors 314 that are available to collect information may allow for more accurate customization of exercise regimens. For example, a fitness machine 102 equipped with a high number of sensors 314 may more accurately assess fitness-related information about the user 104 than a wearable device 106 with fewer available sensors 314.

Figure 4:
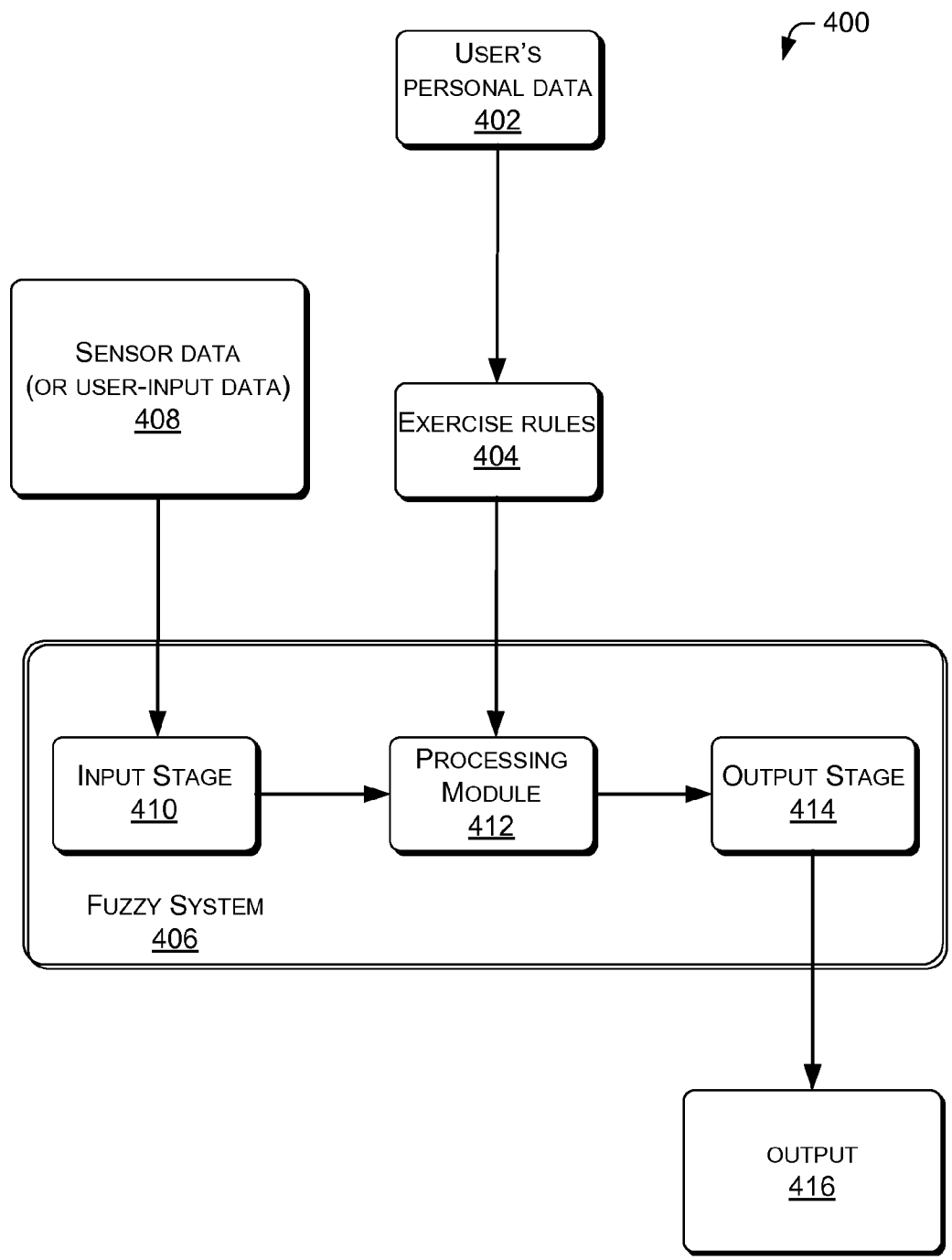
FIG. 4 is a block diagram of a fuzzy processing environment of an example fitness system, according to some embodiments.

FIG. 4 is a block diagram of a fuzzy processing system 400 of an example fitness system, according to some embodiments. For example, fuzzy processing system 400 may reside in the fitness machine 102 and/or the client device 106, shown in FIG. 1. Fuzzy processing system 400 personalizes a user's exercise experience by utilizing personal data about the user and by utilizing data of sensor measurements of the user's past and current exercise sessions. For example, system 400 can collect heart rate and blood pressure measurements of a user during an exercise session and compare these to such measurements from earlier exercise sessions. Considering the weight and age of the user, fitness goals, and frequency of exercise sessions, the system 400 uses a fuzzy system to determine whether to instruct the user to slow or speed up their activity (e.g., slow or speed up their running pace or other repetitive motion) or whether to change operating characteristics of the fitness machine of system 400.

In other examples, system 400 can receive data entered by the user at the beginning of the user's exercise session. Such data can include daily caloric intake, mood, general physical feeling, locations of any aches or pains, and any updated information regarding exercise goals, health history, and so on. In some implementations, system 400 is configured to adjust a duration of an exercise activity based, at least in part, on caloric intake (e.g., during the same day or a number of previous consecutive days) of the user. In some implementations for a treadmill, system 400 is configured to adjust an inclination of the treadmill based, at least in part, on one or more of body weight, heart rate, blood pressure, oxygen level, hydration level, body temperature, blood glucose level, or respiratory rate, just to name a few examples.

In other implementations, system 400 is configured to stop motion of an exercise machine for a time period during which recovery rate of the user is determined based, at least in part, on one or more of body weight, heart rate, blood pressure, oxygen level, hydration level, body temperature, blood glucose level, or respiratory rate. System 400 subsequently restarts the motion of the exercise machine and adjusts operation of the exercise machine based, at least in part, on the determined recovery rate.

In some particular embodiments, a user's personal data 402 and/or exercise rules 404 may be maintained remotely, such as in memory associated with the one or more servers 108(1), 108(2), . . . , 108(N) via network(s) 110. For example, user profile store 114 may include at least some of user's personal data 402, and fitness knowledge store 112 may include at least some of exercise rules 404.

In some embodiments, exercise rules 404 include a set of rules based, at least in part, on the user's personal data 402. For example, such rules can be generated by considering a user's age, weight, exercise goals, history of injuries or diseases, and so on. The exercise rules 404 are provided to a fuzzy system 406 that combines the exercise rules 404 with sensor data or user-input data 408. In some examples, sensor data includes data from one or more sensors 314, such as one or more camera-based sensors 316 that detect image data of a user on the fitness machine 102. In other examples, sensor data 408 includes data from the scanning device 212 of FIG. 2, configured to noninvasively collect various vital measurements from the user 104.

Fuzzy system 406 may be implemented by software executable by processor(s) 302, for example. Fuzzy system 406 includes an input stage 410, a processing module 412, and an output stage 414. The input stage 408 receives a variety of sensor data or user-input data 408, which can be real-time data and/or archived data (e.g., stored in memory in client device 106 and/or memory associated with the one or more servers 108(1), 108(2), . . . , 108(N)).

The input stage 410 maps received sensor data 408 to the appropriate fuzzy membership functions and truth values. The processing module 412 invokes fuzzy rules to generate a result for each rule, and subsequently combines the results of the rules. The output stage 414 converts the combined results into a specific output, which may be provided to a user or to various electronics of a fitness machine via output 416. In some implementations, output 416 may include electronic signals provided to electrical and/or mechanical components of a fitness machine to affect operation of the fitness machine. For example, output 416 can include electronic signals to change inclination and/or speed of a treadmill based, at least in part, on combined results of exercise rules generated by processing module 412. In other implementations, output 416 may include electronic signals provided to a display and/or speakers of a fitness machine to deliver instructions to a user of the fitness machine. For example, output 416 can include electronic signals to display a set of text-based instructions for the user to take corrective action for a particular exercise. Such instructions can be based, at least in part, on combined results of exercise rules generated by processing module 412.

Example User Setup and Exercise Routine

Use of the fitness machine 102 according to the embodiments disclosed herein may begin by initially creating a user profile for the user 104 that may be associated with information about the user 104 and stored in the user profile store 114. The user 104 may use any suitable computing device, such as the client device 106 and/or the fitness machine 102, to input information for profile creation. Such information, as mentioned above, may include a username, password, name, mailing address, phone number, e-mail address, gender, date of birth, race or ethnicity, height, weight, health conditions (e.g., heart disease, cancer, previous strokes, etc.). The user 104 may link other accounts, such as social networking accounts as part of the setup of their user profile in the user profile store 114. The user 104 may provide answers to questionnaires via the client device 106 and/or the fitness machine 102. The client device 106 and/or the fitness machine 102 may be configured to obtain information about the user from other sources, such as a Nike® FuelBand or similar source of fitness related information.

The user 104 may input, via the client device 106 (e.g., an application or browser) or the fitness machine 102 user interface, initial fitness goals, such as to "lose weight", "stay fit", "improve endurance", "train for a race", and/or "recover from injury" so that the fitness machine 102 may prescribe a workout regimen tailored to the user 104. The fitness machine 102 may deduce initial fitness goals based on answers to specific questions provided to the user 104. The user 104 may further specify a current physical health level, diet or daily calorie intake, availability, activity level (casual vs. competitive), workout history, and any pertinent exercise routines that the user 104 may prefer over others.

Once all of the relevant information is collected from the user 104 and a profile is created, the fitness machine 102 and/or the client device 106 may display options of how long a particular workout regimen will take with and without dieting. The user 104 may select an option based on whether he/she desires to change their diet according to the diets specified by the fitness machine 102. Other useful links may be provided to the user 104 to augment the prescribed workout regimen, such as other forms of cross training, weight training, resistance training, and the like.

The following paragraphs describe a plurality of "phases" for a workout program. Any individual phase may be optional, and thereby omitted from the overall set of phases that are implemented. In this sense, some or all of the following phases may be implemented as part of the exercise regimen for a user 104.

Phase I

When the user 104 is ready to begin a first exercise routine prescribed by the fitness machine 102, the user 104 may step onto the fitness machine 102 and a short introduction video may be presented via the display 206 to show what will take place over the course of the prescribed exercise regimen until a goal is achieved. This could be shown each time the user 104 uses the fitness machine 102 and may be skipped by the user 104 after an initial viewing.

The fitness machine 102 may collect, via the sensors 314, current information about the user 104, including current vital measurements. For example, the sensors 314 may collect information including, but not limited to, weight and height (to calculate BMI), resting heart rate, blood pressure, temperature, hydration, resting respiratory rate, blood glucose level, and other suitable health measurements.

The user 104 may be asked a series of questions that are designed to gather subjective input from the user 104. For example, the user 104 may be asked, via questions presented on the display 206 or via the speakers 208, "how do you feel?" with options of "Excellent, Good, Tired, or Sick" as possible answers. The user 104 may be asked "How well did you sleep last night?" with options of "Very well, Fine, Restless, Not well" as possible answers. The user 104 may be asked "Do you have any areas of discomfort?" with an image of a human (e.g., a created avatar) presented on the display 206 for the user 104 to touch the display 206 at the portion of the human image where they currently have discomfort. The user 104 may be asked "When was your last meal?" and "Was it a good meal?" The user 104 may be asked "how much time do you have available to exercise?" The user 104 may be asked "How is your overall fitness?" The user's answers may be provided by various ones of the input devices 306 (e.g., touch screen input, voice input, etc.).

Phase II

When Phase I (Pre-Training) is complete, the fitness machine 102 may proceed to Phase II where the user 104 may be instructed to perform one or more warm up stretches. The output devices 308 may facilitate instructions to the user 104 on how to perform the warm up stretches, such as by showing images, video, and/or text via the display 206 on how the stretch(es) should be performed, perhaps with audible instructions provided by the speakers 208. During the warm up stretching, the user 104 may manipulate any linear-based presentation (e.g., video) by pausing, rewinding, fast-forwarding, stopping, skipping, or other suitable UI controls provided on the touch screen display 206 or another input device 306 (e.g., remote control, voice, etc.). The fitness machine 206 may instruct the user 104 to perform one or more dynamic stretches for a recommended number of times, and may continually monitor the user 104 via the one or more camera-based sensors 316 (e.g., the camera-based sensor 204) to determine an exercise performance condition including the pose of the user 104 to evaluate whether the user 104 is performing the stretches correctly and/or for the recommended number of times. The user 104 may request more stretches from the fitness machine 102, or the user 104 may skip over certain ones of the stretches.

A warm up routine may begin after the user 104 has completed the warm up stretches. The warm up routine may include exercising at a moderate pace (e.g., walking, jogging, etc.) to achieve proper vital levels (e.g., heart rate, respiratory rate, etc.). During the warm up routine, the camera-based sensor(s) 316 may capture movements of the user 104 to determine exercise performance conditions (e.g., body form, pace, etc.) in order to evaluate walking/running form. The user information sensors 318 may monitor other vitals, such as hydration, heart rate, and the like, to detect any concerns. External sensors, such as an e-textile sensor, may detect exercise performance conditions involving weight distribution on the feet of the user 104 to detect any potential concerns with how the user 104 is distributing weight during the warm up routine.

When the user 104 has reached target levels (e.g., 60%-80% of a predetermined heart rate level for exercise), the fitness machine 102 may ask the user 104, via the output device(s) 308, if the user is ready to begin the exercise routine and/or inform the user that their exercise routine will start. The user 104 may specify that they are not ready, and the fitness machine 102 may provide the user 104 with more time to get ready. The user 104 may stop the program entirely at any point in time. If the user 104 stops the program at any time, any data that has been captured by the sensors 314 may be uploaded to the server(s) 108(1)-(N) and stored in the user profile store 114 as part of a workout history of the user's profile.

Phase III

When the exercise routine begins, the user 104 starts exercising according to the exercise routine prescribed by the fitness machine 102. If Phase II (as described above) is skipped or omitted, the prescribed exercise routine of Phase III may include a warm-up portion that may or may not be "transparent" to the user 104. For example, the exercise routine may slowly ramp up to a "full speed" exercise routine by seamlessly transitioning through a warm-up phase. The user 104 may be notified of the warm-up phase before or during the ramp up period, or the system may not provide any notification to the user 104 such that the user 104 may be more or less unaware of the occurrence of a warm-up phase.

The exercise routine may comprise a steady or variable pace or speed, resistance, and/or incline over a prescribed duration of time. During the exercise routine, the fitness machine 102 may continuously monitor the user 104 with the sensors 314. For example, vital information may be monitored over the course of the exercise routine with the user information sensors 318 and/or external sensors provided by the user 104. Additionally, or alternatively, movements of the user 104 may collected by the camera-based sensors 316. For example, body form (e.g., running form) may be monitored by determining the angle or flex of the user's arms, the lateral swing of the user's limbs, angle of the user's head, contact of the user's foot with a running/walking surface, and/or whether the user's torso is erect or lordotic. The camera-based sensors 316 may also be configured to detect and interpret muscle images to determine how tense or relaxed the user's neck, arms, shoulders, and/or hands are while exercising. All of this information may be detected from image data collected by the camera-based sensors 316 to determine an exercise performance condition (i.e., body form, muscle tension, etc.).

In some embodiments, one or more of the user information sensors 318, such as the scanning device 212, may be configured to detect vital information when the user 104 touches the sensor (e.g., places the scanning device 212 to their forehead) for a predetermined period of time, while other ones of the user information sensors 318 may work without the need to have the user 104 touch or wear the sensor 318.

The display 206 may constantly, or periodically, display information regarding the sensed vital information of the user 104, such as heart rate, oxygen level, hydration level, and the like. In some embodiments, color coding may be utilized on the display 206 to indicate an evaluation of exercise performance conditions of the user. For example, text-based vital information can be presented on the display 206 in green font, or with an associated green colored symbol, to indicate ideal or acceptable vital levels, while yellow colored text or symbols may indicate that levels are slightly deviated from ideal or normal/acceptable levels, and red colored text may indicate a warning that vital levels are extreme (e.g., too high or too low). The determination of appropriate vital levels may be based on a performance goal of the user 104, and/or an injury prevention metric. For example, in order for the user 104 to achieve a target heart rate, the heart rate information displayed to the user 104 via the display 206 may indicate that the user's heart rate is too low to achieve the exercise goal for the current routine. As another example, in order to prevent injury to the user 104, the fitness machine 102 may output a hydration level measurement and warn the user 104 (e.g., with red color coding) that their hydration level is too low, and that they need to rehydrate so that the user 104 does not pass out from dehydration.

In some embodiments, the fitness machine 102 may be configured to vary the speed, resistance, incline, and/or duration to help the user 104 achieve target levels of performance or to prevent injury. For example, if a prescribed exercise routine was originally designed to burn a predetermined number of calories or achieve a target heart rate for the user 104, and the fitness machine 102, via the sensors 314, may determine that the user 104 will not achieve target performance levels with the originally prescribed routine, and may adjust speed, resistance, incline, and/or duration of the exercise routine, or otherwise dynamically modify the prescribed exercise routine to help the user 104 achieve goals, or to minimize risk of injury. In some embodiments, the adjustment or modification of the prescribed exercise routine is done automatically by the fitness machine 102, while in other embodiments, feedback or instruction is provided to the user 104 who may then manually adjust or modify the exercise routine themselves (e.g., modify speed, resistance, incline, and/or duration manually).

In some embodiments, the camera-based sensors 316 may interpret movements of the user 104 to indicate an exercise performance condition that the user 104 is running with a certain body form that indicates fatigue. If the user 104 does not correct their body form after a predetermined time following an instruction to correct the user's running form, the fitness machine 102 may slow the speed, resistance, incline, and/or duration to minimize the risk of injury to the user 104.

Phase IV

When the exercise routine is completed, the fitness machine 102 may initiate a cool down program. The cool down program may reduce the speed, resistance, and/or incline in order to reduce the heart rate of the user 104 to a level that is close to the resting heart rate of the user 104 measured during Phase I. In some embodiments, the display 206 may present a video, graphics, or images of cool down stretches recommended for the user 104 to cool down. Other optional cool down programs may be presented to the user 104 for selection, such as sitting and performing static stretches, walking around and hydrating, or other suitable cool down methods.

The cool down program may be implemented similarly to the warm up program in that the display 206 may present audio and video, images, graphics, etc., and the user 104 may pause, skip, rewind, and the like, to control the cool down presentation. Furthermore, the camera-based sensors 316 may collect image data of the user 104 when stretching to determine exercise performance conditions on body form and number of repetitions. This allows the fitness machine 102 to provide constructive feedback for the user 104 to correct body form, for example, if stretches are being performed incorrectly.

Phase V

An end routine may be implemented after cool down that shows a summary of important information via the display 206. In some embodiments, the summary may be uploaded to the cloud (i.e., the server(s) 108(1)-(N)) and/or sent to other computing devices or accounts of the user 104, such as the client device 106 or the user's e-mail, social networking account, and so on. The summary may include, but is not limited to, distance traveled, speed, calories burned, pace, and vital information measured during the exercise routine. Information such as speed, pace, and vital measurements may be presented as a graph (i.e., line graph) over the duration of the workout, and/or presented as average values. The summary may be presented via any suitable device and may give the user 104 the option to select a link for more detailed information containing charts, graphs, tables, etc.

The end routine may further involve asking the user 104 a series of questions, for example, via the display 206 of the fitness machine 102, or via the client device 206. The questions may include, but are not limited to, the following: (a) How do you feel after the workout?; (b) How would you rate the exercise routine?; (c) What went well or not so well with the workout? Answers may be selected from multiple choice options for efficiency purposes.

In some embodiments, the summary may highlight what went well during the exercise routine, such as distance, speed, calories burned, stance, pace, vital information, and the like. The summary may further indicate areas for improvement to be attempted during the next exercise routine.

All information collected during the workout, whether the workout was completed, or whether the user 104 quit or aborted the workout, is uploaded to the server(s) 108(1)-(N) and stored in the user profile store 114. Information uploaded to the cloud may include, but is not limited to, vital measurements, image data, videos of the exercise routine, or any other suitable information. A workout history for the user 104 may be built over time to show fitness performance data that may be analyzed over time to identify trends, or other useful statistics that the user 104 may find valuable. The user 104 may share the uploaded information via social networking sites, with a health care professional, personal trainer, coach, insurance company, or the like.

Example Processes

Figure 5:
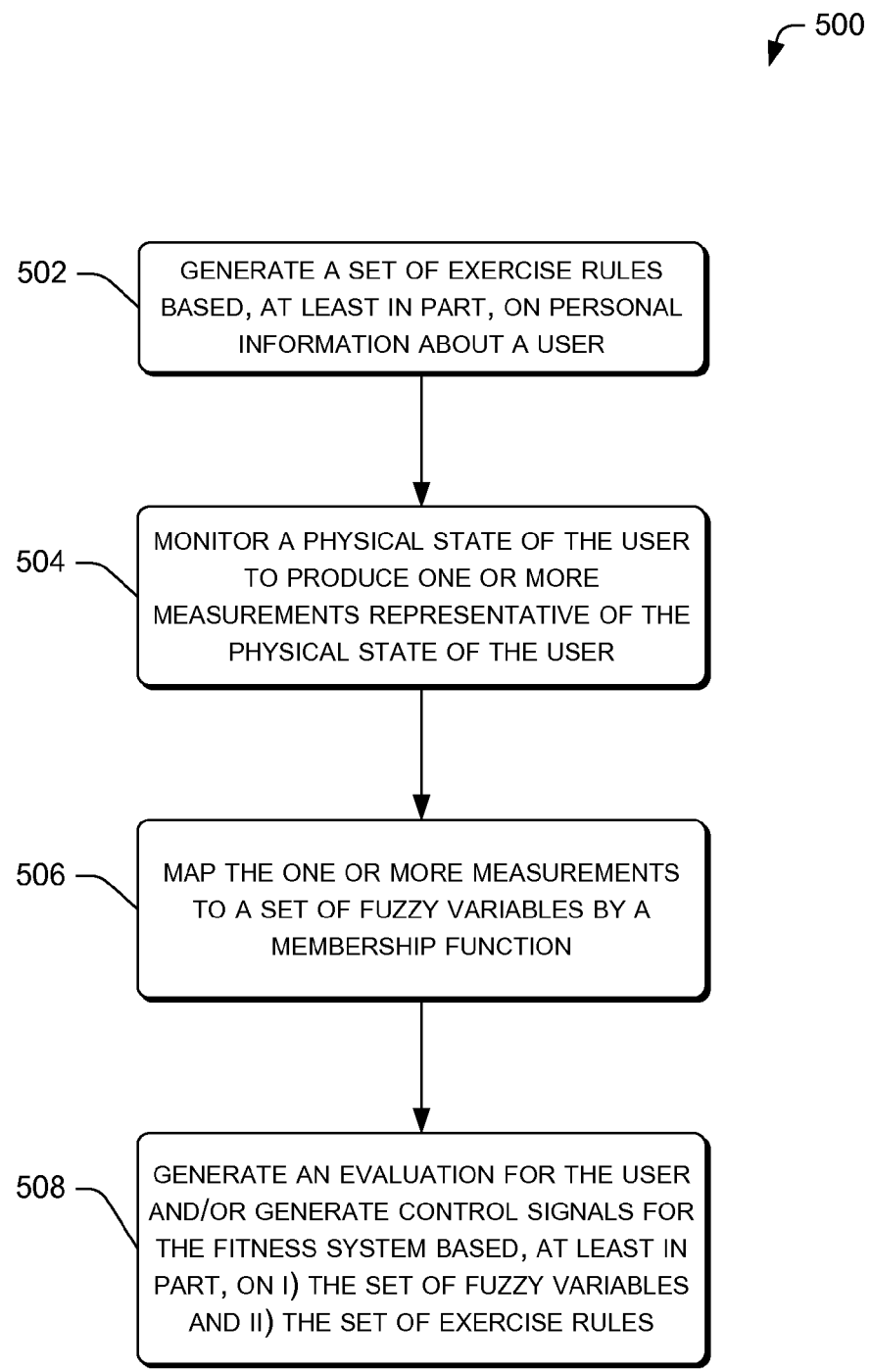
FIG. 5 is a flow diagram of an illustrative process of evaluating an exercise performance condition of a user on an example fitness system of the embodiments disclosed herein.

FIG. 5 is a flow diagram of an illustrative process 500. Process 500 is illustrated as a collection of clocks in a logical flow graph, which represent a sequence of operations that can be implemented in hardware, software, or a combination thereof. In the context of software, the blocks represent computer-executable instructions that, when executed by one or more processors, perform the recited operations. Generally, computer-executable instructions include routines, programs, objects, components, data structures, and the like that perform particular functions or implement particular abstract data types. The order in which the operations are described is not intended to be construed as a limitation, and any number of the described blocks can be combined in any order and/or in parallel to implement the process.

FIG. 5 illustrates a process 500 of evaluating an exercise performance condition of a user 104 of a fitness system 111 (e.g., the fitness machine 102) of the embodiments disclosed herein. Process 500, for example, can be performed by system 100 shown in FIG. 1. It is to be appreciated that, in instances where the fitness machine 102 is not part of the networked fitness system 111, the steps of the process 500 may be performed by any suitable device(s) (e.g., the client device 106) that constitute the networked fitness system 111.

At block 502, a set of exercise rules may be generated based, at least in part, on personal information about a user. The exercise rules may include a set of fuzzy variables (e.g., corresponding to the personal information) each represented by an associated membership function. At block 504, a physical state of the user is monitored to produce one or more measurements representative of the physical state of the user. Such monitoring may be performed by camera-based sensors, noninvasive scanning devices, and e-textile sensors, just to name a few examples. At block 506, the one or more measurements may be mapped to a set of fuzzy variables by a membership function. The fuzzy variables may correspond to any of a number of input data, such as personal data of the user, measurement data from sensors, and so on. At block 508, an evaluation for the user may be generated based, at least in part, on the set of fuzzy variables and the set of exercise rules. Such an evaluation can include an evaluation of exercise performance by the user or an instruction for the user to take corrective action regarding exercise activity. As in a situation described above, for example, a prescribed exercise routine may be originally designed to burn a predetermined number of calories or achieve a target heart rate for the user 104. If, however, the fitness machine 102, via the sensors 314, determines that the user 104 will not achieve target performance levels with the originally prescribed routine, then based on a set of fuzzy variables and the set of exercise rules the fitness machine 102 may adjust speed, resistance, incline, and/or duration of the exercise routine, or otherwise dynamically modify the prescribed exercise routine to help the user 104 achieve goals, or to minimize risk of injury. In some embodiments, such an evaluation can also include other possible exercise routines (e.g., longer duration with lower intensity) as recommendations that the user may consider for a subsequent exercise session.

The environment and individual elements described herein may of course include many other logical, programmatic, and physical components, of which those shown in the accompanying figures are merely examples that are related to the discussion herein.

Other architectures may be used to implement the described functionality, and are intended to be within the scope of this disclosure. Furthermore, although specific distributions of responsibilities are defined above for purposes of discussion, the various functions and responsibilities might be distributed and divided in different ways, depending on circumstances.

Conclusion

In closing, although the various embodiments have been described in language specific to structural features and/or methodological acts, it is to be understood that the subject matter defined in the appended representations is not necessarily limited to the specific features or acts described. Rather, the specific features and acts are disclosed as example forms of implementing the claimed subject matter.

The invention claimed is:

1. A method of evaluating an exercise performance condition of a user of a fitness system, the method comprising:
generating a set of exercise rules based, at least in part, on personal information about the user;
detecting, by a camera-based sensor, image data of the user;
analyzing the image data to produce one or more measurements representative of a muscle tension of the user;
mapping the one or more measurements representative of the muscle tension to a set of fuzzy variables by a membership function; and
generating an evaluation for the user based, at least in part, on i) the set of fuzzy variables and ii) the set of exercise rules.

2. The method of claim 1, further comprising obtaining, based on one or more additional sensors, one or more additional measurements representative of a physical state of the user, the one or more additional measurements including one or more of body weight, heart rate, blood pressure, oxygen level, hydration level, body temperature, blood glucose level, or respiratory rate.

3. The method of claim 1, further comprising analyzing the image data to produce one or more additional measurements relating to a stance of the user.

4. The method of claim 1, further comprising identifying, by the camera-based sensor, the user based at least in part on facial recognition.

5. The method of claim 1, further comprising:
identifying the user; and
downloading from a remote network server the personal information about the user.

6. The method of claim 1, wherein the personal information about the user includes one or more of name, gender, age, race, height, weight, health conditions, or fitness goals.

7. The method of claim 1, wherein the evaluation includes one or more of i) an evaluation of exercise performance by the user or ii) an instruction for the user to take corrective action.

8. The method of claim 7, further comprising causing display of:
an image of a reference user having an ideal exercise form, and an avatar of the user that indicates the exercise performance of the user.

9. The method of claim 8, wherein the causing the display of the avatar of the user comprises overlaying the avatar of the user on top of the image of the reference user.

10. The method of claim 1, wherein the fitness system includes a treadmill, and wherein the evaluation includes one or more of instructions to correct a stance of the user, to correct running stride, or to correct running pace.

11. The method of claim 1, further comprising providing the evaluation on a display in the form of a text-based message of the evaluation.

12. The method of claim 1, further comprising:
detecting, by an electronic textile (e-textile) sensor, pressure forces on at least one foot of the user, wherein the generating the evaluation for the user is further based, at least in part, on the pressure forces.

13. The method of claim 1, further comprising displaying a text-based message of the evaluation for the user.

14. A fitness system comprising:
a camera-based sensor to detect image data of a user;
one or more processors; and
memory, storing instructions that, when executed by the one or more processors, perform operations comprising:
generating a set of exercise rules based, at least in part, on personal information about the user;
analyzing the image data detected by the camera-based sensor to produce one or more measurements representative of a muscle tension of the user;
mapping the one or more measurements representative of the muscle tension to a set of fuzzy variables by a membership function; and
generating an evaluation for the user based, at least in part, on i) the set of fuzzy variables and ii) the set of exercise rules.

15. The fitness system of claim 14, further comprising one or more additional sensors, the operations further comprising obtaining, based on the one or more additional sensors, one or more additional measurements representative of a physical state of the user, the one or more additional measurements including one or more of body weight, heart rate, blood pressure, oxygen level, hydration level, body temperature, blood glucose level, or respiratory rate.

16. The fitness system of claim 14, the operations further comprising analyzing the image data to produce one or more additional measurements relating to a stance of the user.

17. The fitness system of claim 14, the operations further comprising identifying the user based at least in part on facial recognition using the image data detected by the camera-based sensor.

18. The fitness system of claim 14, the operations further comprising:
identifying the user; and
downloading from a remote network server the personal information about the user.

19. The fitness system of claim 14, wherein the personal information about the user includes one or more of name, gender, age, race, height, weight, health conditions, or fitness goals.

20. The fitness system of claim 14, wherein the evaluation includes one or more of i) an evaluation of exercise performance by the user or ii) an instruction for the user to take corrective action.

21. The fitness system of claim 20, further comprising a display, the operations further comprising presenting on the display:
an image of a reference user having an ideal exercise form, and
an avatar of the user that indicates the exercise performance of the user.

22. The fitness system of claim 21, wherein the presenting on the display the avatar of the user comprises overlaying the avatar of the user on top of the image of the reference user.

23. The fitness system of claim 14, wherein the fitness system includes a treadmill, and wherein the evaluation includes one or more of instructions to correct a stance of the user, to correct running stride, or to correct running pace.

24. The fitness system of claim 14, further comprising a display, the operations further comprising providing the evaluation on the display in the form of a text-based message of the evaluation.

25. The fitness system of claim 14, further comprising an electronic textile (e-textile) sensor, the operations further comprising:
detecting, by the e-textile sensor, pressure forces on at least one foot of the user, wherein the generating the evaluation for the user is further based, at least in part, on the pressure forces.

26. The fitness system of claim 14, further comprising a display, the operations further comprising presenting, on the display, a text-based message of the evaluation for the user.

27. A computer-implemented method comprising:
generating a set of exercise rules based, at least in part, on personal information about a user;
detecting, by a camera-based sensor, image data of the user;
analyzing the image data to produce one or more measurements representative of a muscle tension of the user;
mapping the one or more measurements representative of the muscle tension to a set of fuzzy variables by a membership function; and
presenting, on a display, an evaluation for the user based, at least in part, on i) the set of fuzzy variables and ii) the set of exercise rules.

28. The computer-implemented method of claim 27, further comprising obtaining, based on one or more additional sensors, one or more additional measurements representative of a physical state of the user, the one or more additional measurements including one or more of body weight, heart rate, blood pressure, oxygen level, hydration level, body temperature, blood glucose level, or respiratory rate.

29. The computer-implemented method of claim 27, further comprising analyzing the image data to produce one or more additional measurements relating to a stance of the user.

30. The computer-implemented method of claim 27, further comprising:
identifying the user; and
downloading from a remote network server the personal information about the user.

31. The computer-implemented method of claim 27, wherein the personal information about the user includes one or more of name, gender, age, race, height, weight, health conditions, or fitness goals.

32. The computer-implemented method of claim 27, wherein the evaluation includes one or more of i) an evaluation of exercise performance by the user or ii) an instruction for the user to take corrective action.

33. The computer-implemented method of claim 32, further comprising presenting on the display:
an image of a reference user having an ideal exercise form, and
an avatar of the user that indicates the exercise performance of the user.

34. The computer-implemented method of claim 33, wherein the presenting on the display the avatar of the user comprises overlaying the avatar of the user on top of the image of the reference user.

\* \* \* \* \*